(12) United States Patent
Silverman

(10) Patent No.: US 8,801,774 B2
(45) Date of Patent: *Aug. 12, 2014

(54) TUBE WITH REVERSE NECKING PROPERTIES

(71) Applicant: W. L. Gore & Associates, Inc., Newark, DE (US)

(72) Inventor: James D. Silverman, Flagstaff, AZ (US)

(73) Assignee: W. L. Gore & Assoicates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/865,788

(22) Filed: Apr. 18, 2013

(65) Prior Publication Data

US 2013/0238080 A1 Sep. 12, 2013

Related U.S. Application Data

(63) Continuation of application No. 12/503,785, filed on Jul. 15, 2009, now Pat. No. 8,435,282.

(51) Int. Cl.
*A61F 2/06* (2013.01)

(52) U.S. Cl.
USPC .......................................... 623/1.15; 606/108

(58) Field of Classification Search
CPC .............. A61F 2/962; A61F 2/88; A61F 2/82
USPC ............... 623/1.11–1.13, 1.15, 1.23; 606/108
See application file for complete search history.

(56) References Cited

U.S. PATENT DOCUMENTS

| | | |
|---|---|---|
| 3,225,129 A | 12/1965 | Taylor et al. |
| 4,141,364 A | 2/1979 | Schultze |
| 4,411,655 A | 10/1983 | Schreck |
| 4,569,347 A | 2/1986 | Frisbie |
| 4,601,713 A | 7/1986 | Fuqua |
| 4,655,771 A | 4/1987 | Wallsten |
| 4,732,152 A | 3/1988 | Wallsten et al. |
| 4,738,666 A | 4/1988 | Fuqua |
| 4,848,343 A | 7/1989 | Wallsten et al. |
| 4,875,480 A | 10/1989 | Imbert |
| 4,921,479 A | 5/1990 | Grayzel |
| 5,066,298 A | 11/1991 | Hess |
| 5,139,511 A | 8/1992 | Gill et al. |
| 5,171,262 A | 12/1992 | MacGregor |
| 5,171,305 A | 12/1992 | Schickling et al. |

(Continued)

FOREIGN PATENT DOCUMENTS

| | | |
|---|---|---|
| EP | 0 163 525 | 12/1985 |
| EP | 0682922 | 4/1994 |

(Continued)

*Primary Examiner* — Victor Nguyen
(74) *Attorney, Agent, or Firm* — David J. Johns

(57) ABSTRACT

An improved tubular structure adapted to increase in diameter upon application of axial force is provided. Increase in diameter is achieved by constructing the tube from multiple layers of material that move relative to each other during axial elongation of the tube. The tube of the present invention can be used both to avoid problems in "necking" found in many prior tube devices, and to provide additional benefits that increases in diameter of the tube during axial elongation can provide. As such, the tube of the present invention may be useful as a manufacturing aid, as a deployment sheath (for example, to deliver medical devices), and in other applications that may benefit from easier tubular sheath removal.

8 Claims, 5 Drawing Sheets

(56) References Cited

U.S. PATENT DOCUMENTS

| | | | |
|---|---|---|---|
| 5,176,659 | A | 1/1993 | Mancini |
| 5,211,654 | A | 5/1993 | Kaltenbach |
| 5,234,425 | A | 8/1993 | Fogarty et al. |
| 5,318,588 | A | 6/1994 | Horzewski et al. |
| 5,328,469 | A | 7/1994 | Coletti |
| 5,352,236 | A | 10/1994 | Jung |
| 5,364,345 | A | 11/1994 | Lowery et al. |
| 5,382,399 | A | 1/1995 | Moret de Rocheprise et al. |
| 5,395,349 | A | 3/1995 | Quiachon et al. |
| 5,405,377 | A | 4/1995 | Cragg |
| 5,445,646 | A | 8/1995 | Euteneuer et al. |
| 5,447,503 | A | 9/1995 | Miller |
| 5,458,573 | A | 10/1995 | Summers |
| 5,464,419 | A | 11/1995 | Glastra |
| 5,476,508 | A * | 12/1995 | Amstrup ............... 623/1.2 |
| 5,571,135 | A | 11/1996 | Fraser et al. |
| 5,641,373 | A | 6/1997 | Shannon et al. |
| 5,653,697 | A | 8/1997 | Quiachon et al. |
| 5,662,703 | A * | 9/1997 | Yurek et al. ............... 623/1.12 |
| 5,690,644 | A | 11/1997 | Yurek et al. |
| 5,762,604 | A | 6/1998 | Kieturakis |
| 5,789,047 | A | 8/1998 | Sasaki et al. |
| 5,800,456 | A | 9/1998 | Maeda et al. |
| 5,824,041 | A | 10/1998 | Lenker et al. |
| 5,833,699 | A | 11/1998 | Chuter |
| 5,868,707 | A | 2/1999 | Williams et al. |
| 5,893,868 | A | 4/1999 | Hanson et al. |
| 5,993,427 | A | 11/1999 | Rolland et al. |
| 5,997,508 | A | 12/1999 | Lunn et al. |
| 6,025,044 | A | 2/2000 | Campbell et al. |
| 6,039,721 | A | 3/2000 | Johnson et al. |
| 6,042,605 | A | 3/2000 | Martin et al. |
| 6,059,813 | A | 5/2000 | Vrba et al. |
| 6,110,146 | A | 8/2000 | Berthiaume et al. |
| 6,126,685 | A | 10/2000 | Lenker et al. |
| 6,174,328 | B1 | 1/2001 | Cragg |
| 6,238,410 | B1 | 5/2001 | Vrba et al. |
| 6,254,628 | B1 | 7/2001 | Wallace et al. |
| 6,280,412 | B1 | 8/2001 | Pederson et al. |
| 6,352,561 | B1 | 3/2002 | Leopold et al. |
| 6,371,980 | B1 | 4/2002 | Rudakov et al. |
| 6,387,118 | B1 | 5/2002 | Hanson |
| 6,432,130 | B1 | 8/2002 | Hanson |
| 6,447,540 | B1 | 9/2002 | Fontaine et al. |
| 6,468,243 | B1 | 10/2002 | Miyagawa et al. |
| 6,544,278 | B1 | 4/2003 | Vrba et al. |
| 6,547,813 | B2 | 4/2003 | Stiger et al. |
| 6,607,552 | B1 | 8/2003 | Hanson |
| 6,652,492 | B1 | 11/2003 | Bell et al. |
| 6,939,327 | B2 | 9/2005 | Hall et al. |
| 6,942,682 | B2 | 9/2005 | Vrba et al. |
| 7,105,013 | B2 | 9/2006 | Durcan |
| 7,534,250 | B2 | 5/2009 | Schaeffer et al. |
| 7,625,337 | B2 | 12/2009 | Campbell et al. |
| 7,766,820 | B2 | 8/2010 | Core |
| 7,780,630 | B2 | 8/2010 | Jenson et al. |
| 7,780,692 | B2 | 8/2010 | Nance et al. |
| 8,435,282 | B2 * | 5/2013 | Silverman ............... 623/1.15 |
| 2002/0016607 | A1 | 2/2002 | Bonadio et al. |
| 2002/0099431 | A1 | 7/2002 | Armstrong et al. |
| 2002/0116045 | A1 | 8/2002 | Eidenschink |
| 2003/0088309 | A1 | 5/2003 | Iwasaka et al. |
| 2003/0176909 | A1 | 9/2003 | Kusleika |
| 2003/0208223 | A1 | 11/2003 | Kleiner |
| 2004/0044359 | A1 | 3/2004 | Renati et al. |
| 2004/0087968 | A1 | 5/2004 | Core |
| 2004/0143272 | A1 | 7/2004 | Cully et al. |
| 2004/0143315 | A1 | 7/2004 | Bruun et al. |
| 2005/0222576 | A1 | 10/2005 | Kick et al. |
| 2005/0228479 | A1 | 10/2005 | Pavcnik et al. |
| 2005/0245892 | A1 | 11/2005 | Elkins et al. |
| 2005/0246008 | A1 | 11/2005 | Hogendijk et al. |
| 2005/0267568 | A1 | 12/2005 | Berez et al. |
| 2006/0025844 | A1 | 2/2006 | Majercak et al. |
| 2006/0030923 | A1 | 2/2006 | Gunderson |
| 2006/0041302 | A1 | 2/2006 | Malewicz |
| 2006/0074476 | A1 | 4/2006 | Holman et al. |
| 2006/0155357 | A1 | 7/2006 | Melsheimer |
| 2006/0184225 | A1 | 8/2006 | Pryor |
| 2006/0184226 | A1 | 8/2006 | Austin |
| 2006/0200221 | A1 | 9/2006 | Malewicz |
| 2006/0276872 | A1 | 12/2006 | Arbefeuille et al. |
| 2006/0282152 | A1 | 12/2006 | Beyerlein et al. |
| 2006/0287671 | A1 | 12/2006 | Renati et al. |
| 2007/0055338 | A1 | 3/2007 | Dorn |
| 2007/0198077 | A1 | 8/2007 | Cully et al. |
| 2008/0097301 | A1 | 4/2008 | Alpini et al. |
| 2008/0312733 | A1 | 12/2008 | Jordan |
| 2011/0144739 | A1 | 6/2011 | Cattaneo |

FOREIGN PATENT DOCUMENTS

| | | |
|---|---|---|
| WO | 97/02791 | 1/1997 |
| WO | 98/33454 | 8/1998 |
| WO | 00/74584 | 12/2000 |
| WO | 02/38084 | 5/2002 |
| WO | 03/045284 | 6/2003 |
| WO | 2009/002827 | 12/2008 |
| WO | 2010/015370 | 2/2010 |
| WO | 2010/034453 | 4/2010 |

* cited by examiner

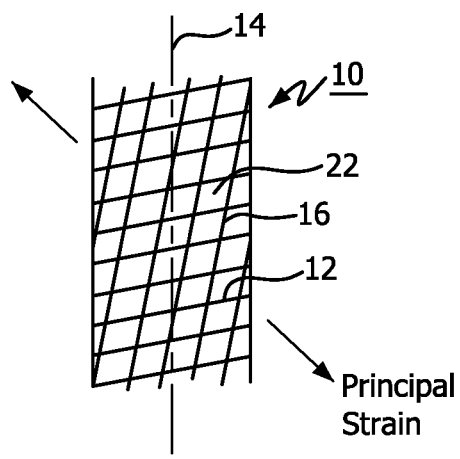
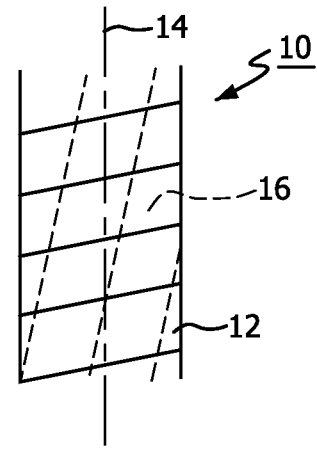
FIG. 5    FIG. 6
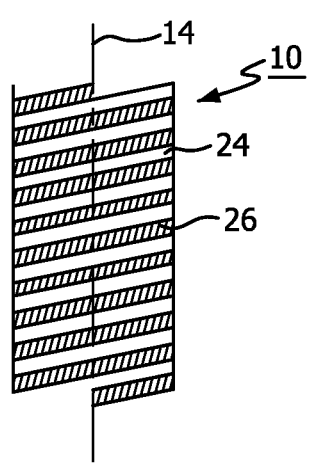
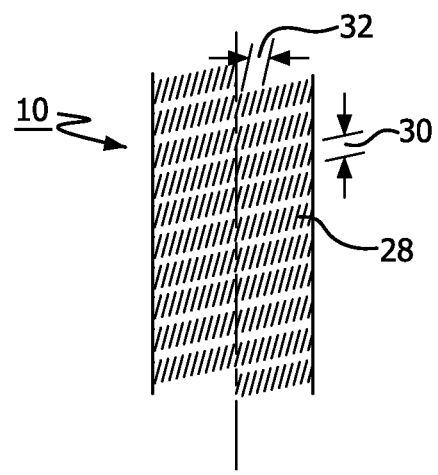
FIG. 7    FIG. 8

TUBE WITH REVERSE NECKING PROPERTIES

CROSS REFERENCE TO RELATED APPLICATIONS

This application is a continuation of U.S. patent application Ser. No. 12/503,785, filed on Jul. 15, 2009, and is incorporated herein by reference in its entirety.

BACKGROUND OF THE INVENTION

1. Field of the Invention

The present invention relates to an improved tubular structure with unique properties suitable for a wide array of applications, including use in manufacturing, as apparatus for positioning and deploying medical diagnostic and treatment devices in a body, and in other uses.

2. Discussion of the Related Art

It is a known property of many tubular constructs, such as those made from flexible plastic materials, that the tube will contract in diameter if the tube is elongated longitudinally. This property is commonly referred to as "necking." Such necking can be problematic in many applications.

For instance, if a plastic wrap is applied over a mandrel in a manufacturing process, pulling on the end of the plastic wrap to remove the wrap from the mandrel will result in the wrap necking down on the mandrel. This often makes it difficult or impossible to slide the plastic wrap off the mandrel, requiring cutting of the wrap or distortion of the mandrel to separate the wrap.

Similarly, necking can likewise be a factor if a plastic tube is used to contain or constrain a device. For instance, in self-expanding medical devices for remote deployment in a patient, such as a stent or blood filter, the device designer must accommodate necking of the plastic tube if it is to be separated from the medical device through the relative sliding of the device and the constraining tube. Typically this requires using plastic tubes that resist necking, such as thicker and/or stiffer materials that can add undesirable profile to the device and/or reduce its flexibility and maneuverability within the body. Optimizing compactness and flexibility are highly desirable as physicians try to reach tighter treatment sites through smaller and more tortuous vessels.

Alternatively, a medical device designer may employ other deployment methods to separate the tube from the implantable device. For instance, a constraining sleeve can be designed to be cut or split from the implantable device, such as is described in U.S. Pat. No. 6,352,561 to Leopold et al. Others have suggested everting the sleeve to reduce the force required to slide the sleeve from the implantable device. Variations on this concept are described in, for instance, U.S. Pat. No. 4,732,152 to Wallsten, U.S. Pat. No. 5,571,135 to Fraser et al., U.S. Pat. No. 6,942,682 to Vrba et al., and US application Ser. No. 2006/0025844 to Majercak et al., and US patent application Ser. No. 2006/0030923 to Gunderson.

While everting sheaths can reduce the tension that must be applied to the constraining sleeve, they still can require considerable tension in order to pull the sheath over itself and the self-expanding device during deployment, resulting mainly from the friction of everted portion of the sheath rubbing against the non-everted portion of the sheath while the sheath is being removed. To whatever degree the sleeve material necks down on the device during deployment, this further complicates device design. These concerns are compounded with longer device lengths and more tightly compacted self-expanding devices that exert greater outward pressures. The greater the tension needed to evert and remove the sheath, the more demanding it is for the medical staff to remove the sheath while trying to hold the apparatus in its exact position during deployment. Increased deployment tensions also require more substantial sheath constructions so as to avoid sheath and deployment line breakage during deployment. It is believed that these deficiencies of everting sheaths may have limited practical applications for such deployment methods.

In co-pending U.S. application Ser. No. 12/014,536 to Irwin et al. (MP/273) a deployment sheath has been proposed that includes diametrically stored material to assist in sheath removal during implantable device deployment. For example, by constructing a constraining sheath with one or more folds or "pleats," it is much easier to evert the sleeve over itself during deployment by allowing the pleats to open as the sheath everts over itself. This essentially produces an inverse effect from necking—as the pleats open, the tubular sheath appears to grow diametrically while it is everting on itself. It has been found that this greatly aids in the deployment process. As a result, such pleated deployment sheaths are believed to be useful in a wide array of medical diagnostic and treatment devices, including stents, stent-grafts, balloons, blood filters, occluders, probes, valves, electronic leads, orthopedic devices, etc.

Plainly pleated tubes can be used not only to address the problem of necking, but actually can allow the tube to increase in effective diameter as axial force is applied to the tube. This is a major advancement over prior medical device deployment apparatus. Nevertheless, providing pleated sheaths with tightly controlled "growth" properties, as is required for medical device deployment, requires careful design and quality assurance controls. Pleated sheaths also work best when deployed in everted tube configurations.

Employing a pleated sheath to constrain and deploy a medical device such as when used as described above, may be desirable but it is recognized that a single layer of material would be preferable for such applications since it further reduces device profile.

Accordingly, it would be desirable to develop a tubular apparatus that is capable of increasing diametrically as axial tension is applied to it.

It would be further desirable to develop such a tubular construct that increases in diameter when axially elongated that can be used in single or multiple layers, both with and without pleats.

SUMMARY OF THE INVENTION

The present invention is directed to an improved tubular structure that is adapted to increase in diameter when axial force is applied to the structure. This increase in diameter may be accomplished by constructing the tube from multiple layers of material that move relative to each other during axial elongation of the tube. The tube of the present invention can be used both to avoid problems in "necking" found in many prior tube devices, and to provide additional benefits that increases in diameter of the tube during axial elongation can provide. As such, the tube of the present invention may be useful as a manufacturing aid, as a deployment sheath (for example, to deliver medical devices), and in other applications that may benefit from easier tubular sheath removal.

In one embodiment of the present invention, the tubular structure comprises a first helical wrap at a first wrap angle and a second helical wrap at a second wrap angle, the tubular structure having a first diameter and a first axial length. When the tubular structure is increased from the first axial length to an elongated second axial length, the first diameter increases to an enlarged second diameter.

In a further embodiment of the present invention, the tubular structure has a longitudinal axis comprising a wrap of at least one tape at a first wrap angle of x, and a wrap of at least one tape at a second wrap angle of y, with both wraps being in the same relative direction. The two wrap angles x and y are both formed at an angle of 0 to 90 degrees relative to the axis of the tubular structure, angle x being an angle different from angle y, and x and y oriented at an acute included angle with respect to each other. When axial force is applied to the tubular structure, both angle x and angle y decrease relative to the longitudinal axis, and the acute included angle between x and y increases. Preferably one or both of the tapes is anisotropic, being relatively non-compliant in the direction of wrap. Constructed in this manner, when the tubular structure is increased from the first axial length to an elongated second axial length, the first diameter increases to an enlarged second diameter.

A further defined construct of the present invention comprises a tubular structure having a first axial length and a first diameter wherein under tension an off-axis strain is formed in the tubular structure. When tension is applied to the tubular structure, the tubular structure assumes a second elongated axial length and an enlarged second diameter.

Further defined, the present invention comprises a tubular device having a tubular structure with at least one helically-oriented element and a diameter. Application of axial force to the tubular device causes the helically-oriented element to at least partially unwind, increasing the diameter of the tubular device.

One of the advantages of the present invention is that it can be utilized as a single layer of uniform thickness. When used, for instance, to deploy medical devices, these properties are believed to provide important benefits over prior everted and/or pleated tubes. However, it should be appreciated that the present invention can be incorporated with either everted or pleated constructs (or both) to provide additional improved properties. In all these various iterations, the present invention provides the benefit of allowing delivery of a remotely deliverable medical device with smaller and more flexible profile, and deployment of the device with less tension and more accurate placement.

As a medical device deployment apparatus, the present invention may be used to deploy a wide variety of devices to diagnose and/or treat patients. Such devices may include stents, stent-grafts, balloons, blood filters, occluders, probes, valves, electronic leads (e.g., pacing or defibrillator leads), orthopedic devices, etc. The deployment apparatus of the present invention may be modified to address many different device delivery and deployment needs. For instance, the number of wraps, the wrap angles, the types of wrap materials, the use of slits or other biasing means, the use of pleats, the orientation of the pleats, the use of sheath eversion, etc., can be adjusted to allow devices to deploy in different manners. Additionally, the sheaths of the present invention can be mounted in a variety of ways on devices to accommodate different deployment requirements, such as allowing a device to deploy off a catheter hub-to-tip, or tip-to-hub, or from a mid-point of a device outward in both directions.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 5 is a schematic representation of a first embodiment of a tube of the present invention;

FIG. 6 is a schematic representation of a second embodiment of a tube of the present invention;

FIG. 7 is a schematic representation of a third embodiment of a tube of the present invention;

FIG. 8 is a schematic representation of the fourth embodiment of a tube of the present invention;

DETAILED DESCRIPTION OF THE ILLUSTRATED EMBODIMENTS

Reference will now be made in detail to an embodiment of the present invention, example of which is illustrated in the accompanying drawings.

The present invention is directed to an improved tubular structure that is adapted to increase in diameter when axial force is applied to the structure. This increase in diameter is preferably accomplished by constructing the tube from multiple layers of material that move relative to each other during axial elongation of the tube.

In its simplest form, the tubular structure of the present invention comprises a first helical wrap at a first wrap angle and a second helical wrap at a second wrap angle, the tubular structure having a first diameter and a first axial length. When the tubular structure is increased from the first axial length to an elongated second axial length, the first diameter increases to an enlarged second diameter. This concept is best illustrated in the model shown in FIGS. 1 and 2.

Figure 1:
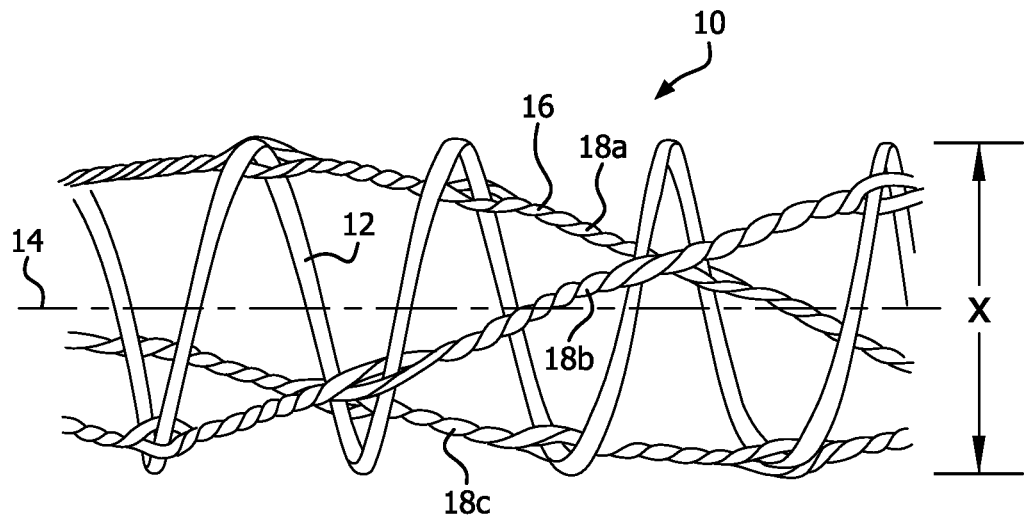
FIG. 1 is an elevation view of a schematic model demonstrating the concept of the present invention, in an unstrained configuration.

FIG. 1 shows a model 10 comprising a first helical structure 12, in the form of a permanently elongated SLINKY® spring toy, presenting a first wrap angle from axis 14. A wrap of a second helical structure 16, in the form of three strings 18a,

18b, 18c, is attached at approximately equidistant points around the first helical structure 12. In this first unstrained configuration the model comprises a first diameter x.

Figure 2:
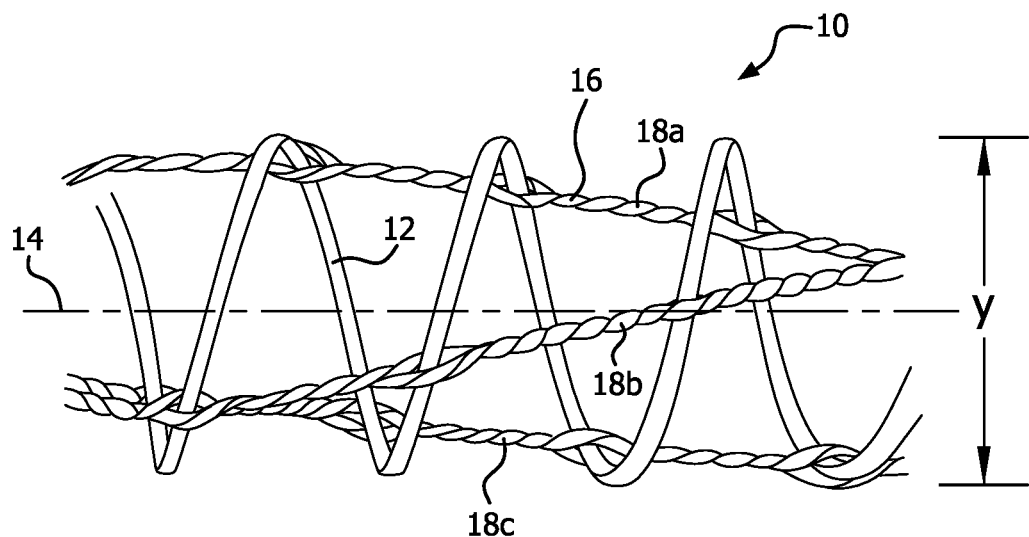
FIG. 2 is an elevation view of the schematic model of FIG. 1 with the model undergoing axial load, demonstrating an increase in the diameter of the model as the model elongates.

FIG. 2 shows the same model 10 with axial force applied to the structure, causing it to elongate. The effect of this elongation is that the angle of the second helical structure 16 reduces relative to the axis 14. This has the effect of essentially "untwisting" the first helical structure 12. This relative movement of the first helical structure causes the model 10 to grow radially to a second, enlarged diameter y.

Figures 3, 4:
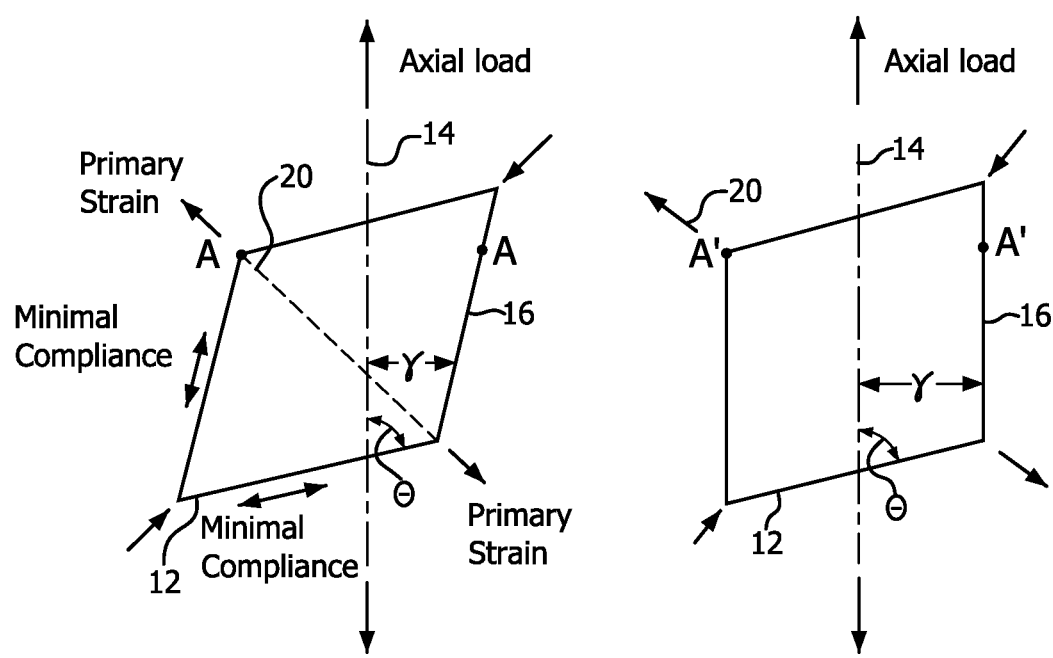
FIG. 3 is a diagram illustrating the relative orientations of the components of the present invention in a first, unstrained configuration.
FIG. 4 is a diagram illustrating the relative orientations of the components of the present invention is a second, strained configuration under an axial load.

This phenomenon may be further understood by reference to diagrams of FIGS. 3 and 4. FIG. 3 is a diagram illustrating in two dimensions a parallelogram element defining the relative orientations of the components of the present invention in a first, unstrained configuration. The axis of the tubular structure is defined by line 14. A first component 12 wrap angle is defined by angle $\Theta$ from axis 14. A second component 16 wrap angle is defined by angle $\gamma$ from axis 14. As is noted in FIG. 3, it is desirable that the first and second components 12, 16 to have minimal compliance along their respective wrap angles $\Theta$ g. Oriented in this manner, the direction of primary strain in this structure is along line 20. The circumference (diameter) of this tube is defined by the distance between points A-A.

When axial load is applied along line 14 to the structure of FIG. 3, the resulting reorientation of the structure is illustrated in FIG. 4. As the tube elongates, angle $\gamma$ will decrease. The circumference as defined by line A'-A' will accordingly increase until angle $\gamma$ eventually reaches zero (0).

By constructing a tube in this manner, it has been determined that tubes can be designed that can provide increases in diameter during elongation of 5, 10, 15, 20, 25% or more. Even greater diameter changes may be possible, with increases of 30, 35, 40, 45, 50% or more being readily achievable. Theoretically, even more substantial diameter changes of 100% to 500% to 1000% or more may be achieved, restricted by practical material and application limitations, such as true strain off of the oriented axis, wall thinning, axial lengthening, lack of oriented strength, etc. as the angles converge and approach the axis.

There are numerous options for creating a tube of the present invention. Preferably the tube comprises two or more unidirectional bias wraps of material at different angles around the intended axis. Preferably, the angle $\Theta$ of the first component is between about 0 and 90 degrees from the tube axis, with about 45 to 85 degrees being more preferred, and about 60 to 80 degrees being most preferable. Likewise, angle $\gamma$ of the second component is between about 0 and 90 degrees from the tube axis, with about 10 to 80 degrees being more preferred, and about 20 to 60 degrees being most preferable. Overall, the small pitch, large wrap angle $\Theta$ component 12 provides hoop strength to the tube; the large pitch/small wrap angle $\gamma$ component 16 provides axial strength and limits axial strain.

For some applications it may be desirable to include additional wraps of three, four, five, or more layers of material to provide additional strength, more thickness or cushioning, modified permeability, or other application-specific desirable properties.

The components of the tube of the present invention may take numerous forms. For most applications it is preferred to employ tapes of material that provided oriented strength and minimal compliance in the direction of their respective wrap angles. The first component should be fixed to the second component such that a change in angle of the first component produces a resulting change in angle of the second component relative to the longitudinal axis of the tube. Off of their wrap angles, for many applications it is preferable to have a more compliant material that will allow the orientation of the two active components to change relative to each other so as to provide maximum diameter growth during axial elongation. Suitable materials for use in the present invention may include, without limitation, fluoropolymers (especially polytetrafluoroethylene (PTFE) and fluorinated ethylene propylene (FEP)), polyethylenes, polyethylene teraphthalate (PET), nylon, polyurethane, polypropylene, polyester, polyimide, etc., as well as composite materials combining these and/or other materials to achieve the desired strength and compliance characteristics. Expanded PTFE (ePTFE) is believed to be most preferred for many applications since it provides excellent axial strength in the direction of expansion but is readily compliant in a direction perpendicular to the direction of expansion.

Depending on applications, tubes of the present invention may be constructed from a continuous material, such as continuous films, tapes, or sheets of materials. Alternatively, the inventive tubes may include discontinuous structures, such as sheets or tapes that include holes or slits therein, or even materials formed from weaves, knits, or other open structures.

Without intending to limit the scope of the present invention, FIGS. 5 through 8 illustrate various embodiments that may be useful to practice the present invention.

FIG. 5 illustrates an embodiment of the present invention that comprises a fully open mesh tube 10. In this embodiment first component 12 and second component 16 each comprises a fiber or wire material. Open spaces 22 are provided between the two components 12, 16 that can be left unfilled or can be covered with a layer of other material (for example, a continuous or discontinuous film). Suitable materials that may be used as one or the other or both of components 12, 16 may include metals such as steel, nitinol, etc., polymers such as nylon, ePTFE, etc. As has been noted, with the right selection of components 12, 16 and with spaces 22 left unencumbered, this construction is believed to provide optimal growth characteristics in accordance with the present invention.

FIG. 6 illustrates an embodiment of a tube 10 of the present invention that comprises a biased wrapped tube of two film (or "tape") components 12, 16. Preferably the two tape components are uniaxially oriented materials with minimal shear and transverse strength. As has been discussed above, ePTFE is particularly desirable for use as one or both of these components.

FIG. 7 illustrates yet another embodiment of a tube 10 of the present invention. This embodiment employs a fine pitch angle helix of full density, high modulus film 24, such as a polyimide, and a low angle pitch of uniaxial film 26, such as ePTFE.

FIG. 8 illustrates still another embodiment of the present invention. In this embodiment the tube 10 comprises a homogenous material with both high and low angle orientations defined by oriented slits 28 in the homogenous material. Low angle component slits are oriented in helical rows 30 around the circumference of the tube, while high angle component slits are defined as diagonals lines 32 across the low angle rows 30.

The above examples are only a few of the many various orientations of the present invention that can be constructed. For example, it should be appreciated that many of the properties of the various embodiments of FIGS. 5 through 8 can be combined, such as constructing a tube with both the continuous material of FIG. 6 combined with selected open spaces of FIG. 5, or combining the high modulus film of FIG. 7 with any of the other three constructs, or employing oriented slits of FIG. 8 on part or all of any of the other three constructs, etc.

The tube of the present invention can be used both to avoid problems in "necking" found in many prior tube devices, and to provide additional benefits that increases in diameter of the tube during axial elongation can provide. As such, the tube of the present invention may be useful as a manufacturing aid, as a deployment sheath (for example, to deliver medical devices), and in other applications that may benefit from easier tubular sheath removal.

Figure 9:
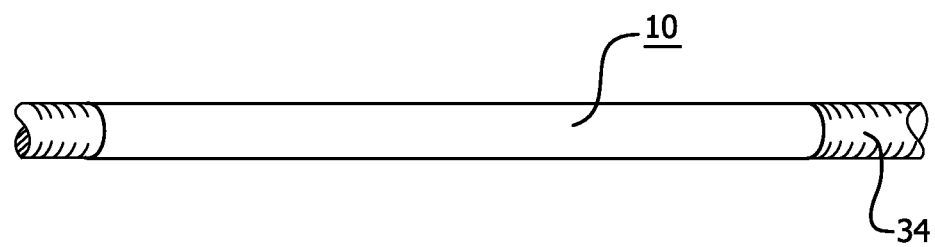
FIG. 9 is a plan view of a tube of the present invention mounted over a mandrel.

FIG. 9 illustrates one such application wherein the tube 10 is mounted on a manufacturing mandrel 34, such as those commonly employed to construct various tubular structures (e.g., taped-wrapped vascular graft components). Heating or other processing steps can shrink the tube around the mandrel, making it difficult or impossible to slide the tube off the mandrel once the manufactured article is removed. With the tube of the present invention, axial movement of the tube 10 causes it to diametrically grow, making its removal from the mandrel much easier. This property may also be highly beneficial in assisting in removing a manufactured article from a mandrel.

Figure 10:
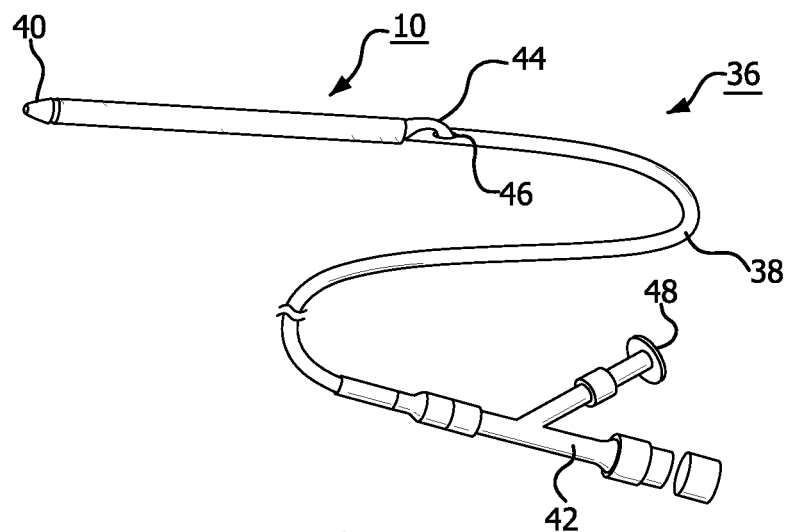
FIG. 10 is a plan view of an embodiment of a tube of the present invention employed in a medical device deployment system mounted near a distal end of a delivery catheter.

Shown in FIG. 10 is one embodiment of a tube 10 of the present invention mounted as a containment sheath near the end of a medical device deployment system 36. The deployment system comprises a catheter shaft 38 extending from a distal olive 40 to a control hub 42. A medical device, such as a stent, stent-graft, balloon, blood filter, occluder, probe, valves, etc., may be contained in the sheath 10 to be deployed at a treatment site within a patient's body. The sheath 10 may be everted over itself to form two layers, an exterior segment that partially or completely covers an interior segment. The tube 10 is attached to a deployment line 44 that is fed into the catheter shaft through opening 46. The deployment line 46 is operatively connected to a deployment knob 48 on the hub 42.

The tube 10 made in accordance with the present invention may be formed from any material that is sufficiently strong both to constrain the device to be delivered and to withstand the tension of the removal process. It is desirable that the sheath 10 also be as thin and lubricious as possible so as to maintain a small device delivery profile and to facilitate the removal process. Since the tube 10 is placed temporarily deep within a patient during delivery and deployment, it is likewise desirable that the sheath be formed from a biocompatible material. As is explained in greater detail below, suitable sheath materials may include: polytetrafluoroethylene (PTFE); expanded PTFE (ePTFE); fluorinated ethylene propylene (FEP), polyethylene teraphthalate (PET), nylon, polyurethane, polypropylene, polyester, etc.

In order to actuate the deployment line 44, medical personnel will unscrew the deployment knob 48 and pull on the knob and connected deployment line to cause the tube 10 to progressively withdraw off of the contained device. If the tube 10 is everted over itself, as the exterior segment of the tube is withdrawn, the tube of the present invention will progressively increase in diameter, steadily everting the interior segment so that it becomes the exterior segment of the tube. The diametrical growth of the tube 10 of the present invention aids in the process of everting, since the exterior segment of the tube 10 will form a larger diameter than the unstrained interior segment. As a result, the larger diameter exterior segment slides easily over the interior segment and is readily removed with minimal friction between the two layers.

Figure 11:
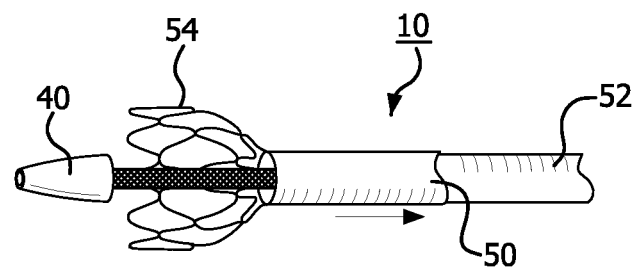
FIG. 11 is an enlarged perspective view of a distal end of a delivery catheter showing tube of the present invention being withdrawn, progressively releasing a self-expanding stent contained therein.

The process of device delivery can be better seen in FIG. 11. In this embodiment, an exterior segment 50 is shown withdrawing over an interior segment 52, shown exposed in cut-away. As the larger diameter exterior segment 50 is withdrawn, the axial force opens up the tube 10 of the present invention. As the tube 10 is withdrawn in this manner, a constrained self-expanding stent 54 is progressively deployed from this embodiment.

It should be appreciated that medical device deployment using the present invention may be accomplished as a single layer or in an everted manner as discussed above. When employing an everted embodiment, in the final construct the exterior segment should have an inner diameter that is sufficiently greater than the outer diameter of the interior segment in order to minimize friction between the two segments. That is, in order to minimize interference between the interior segment and the exterior segment, the axially elongated exterior segment should enlarge enough so that its inner diameter comfortably clears the outer diameter of the unstrained interior segment. It is preferred that the inner diameter of the exterior segment be 0.1 to 50% larger than the outer diameter of the interior segment, and more preferably 10 to 20% larger.

For example, to achieve these dimensions, a tube with a wall thickness of about 0.08 mm and an exterior segment inner diameter of about 2.1 mm will typically be provided with a unstrained interior segment having an outer diameter of about 1.9 mm.

The tube of the present invention is believed to vastly reduce the amount of tension required to deploy a device.

The advantages of the tube of the present invention are believed to be readily adaptable to improve many other devices and processes. One example of such improved combination is to employ the tube of the present invention with the pleated tube deployment constructs that are disclosed in co-pending U.S. patent application Ser. No. 12/014,538 to Irwin et al. filed Jan. 15, 2008, incorporated herein by reference. In this regard, the tube of the present invention can be used with one or more pleats to aid in device delivery and provide further beneficial results.

The invention of the present invention is believed to have many other useful applications, including angioplasty devices, retrieval devices, implantable filters, stents, compliant grafts, etc. It should be noted that the present invention may be scaled to virtually any dimensions.

EXAMPLES

Without intending to limit the scope of the present invention, the following examples illustrate several embodiments of how the present invention may be practiced.

Example 1

Uniaxially Oriented ePTFE Film

This Example describes the assembly of an ePTFE tube that can be easily removed from an assembly mandrel. On a 0.136" steel mandrel a 1" wide expanded polytetrafluroethylene (ePTFE) film (having longitudinally oriented strength, minimal transverse and shear strength, and with FEP on one side functioning as an adhesive) was wrapped at 40° pitch relative to the mandrel axis in a right handed helix orientation with the FEP facing away from the mandrel. Next, a 0.25" wide ePTFE film was wrapped at a 74° pitch in a right handed helix orientation over of the first film with the FEP facing toward the mandrel. The assembly was then thermally processed on-mandrel at a temperature of 320° C. for 13 minutes. The tube was easily removed from the mandrel and no necking was observed at loads below material yield strength.

Example 2

Uniaxially Oriented ePTFE Film with Polyimide Film

This Example describes the assembly of an ePTFE tube comprising a non-compliant polyimide film (Kapton®) between the ePTFE layers. On a 0.236" steel mandrel a 1.0" wide ePTFE film was wrapped at a 56° pitch relative to the mandrel axis in a right handed helix orientation with the FEP facing away from the mandrel. Next, a 0.050"×0.001" polyimide film was wrapped at 82° pitch relative to the mandrel axis at a right handed helix orientation over of the first film. Then a 1" wide ePTFE film was wrapped at a 56° pitch relative to the mandrel axis at a right handed helix orientation on top of the polyimide film with the FEP facing toward the mandrel. The assembly was then thermally processed on-mandrel at a temperature of 320° C. for 13 minutes, after which tube was removed from the mandrel.

The non-compliant polyimide film used for high angle wrap limits axial strain and allows the use of a higher angle ePTFE wrap. The higher angle ePTFE wrap increases the "unwinding" effect for a given axial load. The diameter defined by polyimide wrap grows with axial tension but necking can be observed on the ePTFE between the polyimide.

Example 3

Uniaxially Oriented ePTFE Film with Polyimide Film

To see if the tube made in Example 2 can be modified to reduce necking, slits were created with a knife into the ePTFE in an orientation parallel that of the film structure (56° pitch relative to the mandrel axis), with approximately 0.050" spacing between the slits. These slits eliminate "off-axis" strength of ePTFE film allowing diametric growth of the polyimide helix under tension without ePTFE necking. Thus, the introduction of these slits eliminates necking.

Example 4

Uniaxially Oriented ePTFE Film

This Example describes the assembly of the ePTFE tube as described in Example 1 but on a scaled down version. On a 0.075" steel mandrel, a 0.25" wide ePTFE film was wrapped at a 25° pitch relative to the mandrel axis in a right handed helix orientation with the FEP facing away from the mandrel. Next, at 0.125" wide type ePTFE film wrapped at a 75° pitch relative to the mandrel axis in a right handed helix orientation with the FEP facing toward the mandrel. The assembly was then thermally processed on-mandrel at a temperature of 320° C. for 13 minutes. This construct was removed from the mandrel and was used as a device constraint which was everted for deployment.

Example 5

Uniaxially Oriented ePTFE Film with Polyimide Film

This Example describes the assembly of a tube which is nearly continuous polyimide which responds well to axial tension and returns to the starting diameter with little relative force. On a 0.083" steel mandrel, a 0.25" wide ePTFE film was wrapped at a 28° pitch angle relative to mandrel axis at a right handed helix orientation with the FEP facing away from the mandrel. Next, a 0.043"×0.001" polyimide film was wrapped at 68° pitch angle relative to mandrel axis in a right handed helix orientation over the first film. Then a 0.25" wide ePTFE film was wrapped at a 28° pitch angle relative to mandrel axis in a right handed helix orientation over the polyimide film with the FEP facing toward the mandrel. The assembly was then thermally processed on-mandrel at a temperature of 320° C. for 13 minutes.

Next, the tube was transferred to a 0.075" steel mandrel and the polyimide helix was "twisted down" or "coiled" to eliminate clearance between tube and mandrel, effectively increasing pitch angles for all the wraps. The tube was then compression wrapped with ePTFE film to immobilize it on the mandrel and thermally processed for 7 minutes at 320° C. after which the compression wrap was removed. The resultant tube is nearly continuous polyimide and responds well to axial tension, returning to the starting diameter with little relative force.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A tubular structure having a longitudinal axis comprising
   a wrap of at least one tape at a first wrap angle of x, and a wrap of at least one tape at a second wrap angle of y, with both wraps being in the same relative direction;
   x and y both formed at an angle of about 0 to 90 degrees relative to the axis of the tubular structure;
   x being an angle different from y, and x and y oriented at an acute included angle with respect to each other;
   wherein when axial force is applied to the tubular structure, both x and y decreases relative to the longitudinal axis, and the acute included angle between x and y increases; and
   the tubular structure having a first diameter and a first axial length, wherein when the tubular structure is increased from the first axial length to an elongated second axial length, the first diameter increases to an enlarged second diameter.

2. The tubular structure of claim 1 wherein the tubular structure comprises a sheath containing a self-expanding device.

3. The tubular structure of claim 2 wherein the self-expanding device comprises an implantable medical device.

4. The tubular structure of claim 3 wherein the implantable medical device comprises a stent.

5. The tubular structure of claim 1 wherein the tubular structure comprises a manufacturing aid used in conjunction with a mandrel.

6. The tubular structure of claim 1 wherein the second diameter is at least 5 percent larger than the first diameter.

7. The tubular structure of claim 1 wherein the second diameter is at least 10 percent larger than the first diameter.

8. The tubular structure of claim 1 wherein the second diameter is at least 15 percent larger than the first diameter.

* * * * *